United States Patent
Druon et al.

(10) Patent No.: US 10,501,722 B2
(45) Date of Patent: Dec. 10, 2019

(54) METHOD FOR OPTIMIZING THE PRODUCTION EFFICIENCY, ORGANOLEPTIC QUALITY AND STABILITY OVER TIME OF A PROTEIN-RICH MICROALGAE BIOMASS

(71) Applicant: Corbion Biotech, Inc., South San Francisco, CA (US)

(72) Inventors: Amandine Druon, Lille (FR); Samuel Patinier, Quesnoy-sur-Deule (FR); Béatrice Toursel, Gonnehem (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 15/945,658

(22) Filed: Apr. 4, 2018

(65) Prior Publication Data

US 2018/0223247 A1 Aug. 9, 2018

Related U.S. Application Data

(63) Continuation of application No. 14/910,884, filed as application No. PCT/FR2014/051918 on Jul. 24, 2014, now abandoned.

(30) Foreign Application Priority Data

Jul. 25, 2013 (FR) ...................... 13 57326
Mar. 25, 2014 (FR) ...................... 14 52486

(51) Int. Cl.
| | | |
|---|---|---|
| *C12P 1/00* | (2006.01) | |
| *C12N 1/12* | (2006.01) | |
| *C12N 1/00* | (2006.01) | |
| *C12N 1/02* | (2006.01) | |
| *C12N 1/06* | (2006.01) | |

(52) U.S. Cl.
CPC .............. *C12N 1/12* (2013.01); *C12N 1/005* (2013.01); *C12N 1/02* (2013.01); *C12N 1/066* (2013.01)

(58) Field of Classification Search
CPC ................................. C12P 1/00; C12P 7/6436
See application file for complete search history.

(56) References Cited

U.S. PATENT DOCUMENTS

| | | |
|---|---|---|
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2012/0128851 A1 | 5/2012 | Brooks et al. |
| 2013/0122180 A1 | 5/2013 | Brooks et al. |

FOREIGN PATENT DOCUMENTS

| | | |
|---|---|---|
| CN | 200810240949 A | 12/2008 |
| CN | 101 429 467 | 5/2009 |
| JP | S53-038652 A | 4/1978 |
| WO | WO 2010/045368 A2 | 4/2010 |
| WO | WO 2010/120923 A1 | 10/2010 |
| WO | WO 2011/130578 A2 | 10/2011 |
| WO | WO 2014/117163 A1 | 7/2014 |

OTHER PUBLICATIONS

Huang et al., "Disruption of Chlorella vulgaris cells for the release of biodiesel-producing lipids: a comparison of grinding, ultrasonication, bead milling, enzymatic lysis, and microwaves," Appl Biochem Biotechnol 164: 1215-1224, 2011.
Database WPI, Week 200942, Thomson Scientific, London, GB, AN 2009-J46993, XP-002730563, pp. 1-3.
Written Opinion, dated Oct. 17, 2014, in International Application No. PCT/FR2014/051918, pp. 1-6.
Chacón-Lee et al., "Microalgae for "Healthy" Foods—Possibilities and Challenges," *Comp. Rev. Food Sci. and Safety*, 9: 655-675 (2010).
"Enter the World of Microalgae," Roquette (Jun. 2014).
International Bureau, International Search Report in International Application No. PCT/FR2014/051918, dated Jul. 23, 2019.

*Primary Examiner* — Rosanne Kosson
(74) *Attorney, Agent, or Firm* — Leydig, Voit & Mayer

(57) ABSTRACT

The present invention relates to a method for optimising the downstream processing of a protein-rich microalgae biomass of the *Chlorella* genus previously prepared by fermentation in heterotrophic conditions and in the absence of light, comprising: 1) providing biomass comprising more than 50% protein by dry weight of biomass; next, at low temperature, carrying out the following steps: 2) harvesting the biomass at the end of fermentation, 3) washing and concentrating the biomass, 4) optionally, lysing the biomass, next, without low temperature stress, 5) optionally, concentrating the biomass slurry, 6) applying heat treatment, 7) drying the biomass obtained in this way in order to obtain the product, a step of adjusting the pH to 7 being applied before or after the heat treatment step 6).

13 Claims, No Drawings

METHOD FOR OPTIMIZING THE PRODUCTION EFFICIENCY, ORGANOLEPTIC QUALITY AND STABILITY OVER TIME OF A PROTEIN-RICH MICROALGAE BIOMASS

CROSS-REFERENCE TO RELATED APPLICATIONS

This application is a continuation of U.S. patent application Ser. No. 14/910,884, filed Feb. 8, 2016, entitled "METHOD FOR OPTIMISING THE PRODUCTION EFFICIENCY, ORGANOLEPTIC QUALITY AND STABILITY OVER TIME OF A PROTEIN-RICH MICROALGAE BIOMASS", which is the U.S. National Stage Application of International Patent Application No. PCT/FR2014/051918, filed Jul. 24, 2014, which claims the priority of French Patent Application No. 1452486, filed Mar. 25, 2014 and French Patent Application No. 1357326, filed Jul. 25, 2013.

The present invention relates to a method for optimizing the production efficiency, the organoleptic quality and the stability over time of a protein-rich microalgal biomass, said microalgae being of the *Chlorella* genus, more particularly *Chlorella vulgaris, Chlorella sorokiniana* or *Chlorella prototothecoides*.

PRESENTATION OF THE PRIOR ART

It is well known to those skilled in the art that chlorellae are a potential source of food, since they are rich in proteins and other essential nutrients.

They contain in particular 45% proteins, 20% fats, 20% carbohydrates, 5% fibers and 10% minerals and vitamins.

The use of microalgae (and mainly their proteins) as foodstuff is being increasingly considered in the search for alternative sources to meet the increasing global demand for animal proteins (as reported by the FAO).

Moreover, the European Union has been suffering from a structural deficit in plant proteins for years now, which has amounted in recent years to more than 20 million tons of soy equivalent, currently imported from South America.

The mass production of certain protein-rich microalgae is thus envisioned as a possible way to reduce this "protein deficit".

Extensive analyses and nutritional studies have shown that these algal proteins are equivalent to conventional plant proteins, or even are of superior quality.

Nonetheless, due to the high production costs and technical difficulties in incorporating the material derived from microalgae into organoleptically acceptable food preparations, the widespread distribution of microalgal proteins is still in its infancy.

Microalgal biomasses from various species having a high percentage of proteins have been reported (see table 1 in Becker, *Biotechnology Advances* (2007), 25:207-210).

Additionally, a certain number of patent applications in the prior art, such as patent application WO 2010/045368, teach that it is possible to adjust the culturing conditions so as to further increase the protein content of the microalgal biomass.

Preferably, for the microalgae which have this capacity, the culturing is carried out heterotrophically, in the absence of light and in the presence of an assimilable source of carbon.

These routes for heterotrophic growth make it possible both to mass-produce microalgae and to improve the organoleptic quality thereof by inhibiting the synthesis by the microalga of chlorophyll, which is the source of the pronounced green tea flavor in food preparations containing same.

To enrich the protein content, the microalga is cultured in a nitrogen-enriched medium in the presence of an abundant source of carbon such as glucose. In this case, it is of no concern whether the nitrogen is provided by organic or inorganic sources.

The microalgal biomass produced in this way typically contains at least 40%, or even up to 50-60% proteins by dry cell weight.

However, nothing should be taken for granted in the sense that, as well as the work carried out for the upstream processes for producing protein-rich biomasses—in particular research into suitable fermentation conditions—other difficulties arise from the downstream processing of said biomass to incorporate it into food preparations of interest.

Conventionally, the downstream processing comprises several steps:
 collecting the microalgae separated from their growth medium,
 pasteurization and washing,
 optionally breaking the cells open to release the molecules of interest from them,
 drying.

The first step of collecting the cells is carried out using one or more steps of solid/liquid separation.

The biomass is usually collected by sedimentation, centrifugation or filtration, and sometimes an additional flocculation step is necessary.

Following this first step, which may enable the biomass to be concentrated by 50 to 200 times, the microalgal suspension must be processed rapidly, otherwise it will rapidly break down.

A first operation consists in pasteurizing said suspension, that is to say heating it so as to limit or inhibit the microbial load (growth of contaminating bacteria) but also so as to inactivate certain enzymes liable to cause undesirable odors or flavors ("off flavors").

This operation is conventionally carried out at high temperature for a short time (what is referred to as a "high temperature/short time"—HTST—or ultra-high temperature—UHT—process).

A second operation is washing, recommended on intact cells (with volumes of distilled or deionized water) so as to eliminate soluble impurities.

In the event that a step of breaking open or rupturing the cells is envisioned, several routes are possible: mechanical (homogenizers, bead milling, ultrasonic milling) or non-mechanical (alkaline route, cycles of freezing/thawing, organic solvents or osmotic shock).

The method is chosen as a function of the nature of the microalgal cell wall which is to be broken, and the nature of the product which is to be isolated.

The last downstream treatment step consists in dehydrating said suspension (intact or lyzed cells). Several methods have been employed to dry microalgae of the *Chlorella, Scenedesmus* and *Spirulina* genera. The most conventional are spray drying, drying on a drying drum, and freeze drying. Spray drying is the method most often used on an industrial scale.

However, the sensitivity of certain biomasses to oxidation makes the addition of antioxidants necessary.

Despite this diversity in methods and in combinations of methods suitable for microalgae, there remain six main difficulties (listed a) to f) below) which have not yet been satisfactorily resolved by those skilled in the art, in particular:
a) the loss of protein yield during the downstream processing,
b) the regrettable loss of protein content after the step of heat deactivation of the biomass (which may result in up to 25% loss),
c) the generation of uncontrolled undesirable flavors or odors (off notes) despite the recommended washing steps,
d) the as yet inexplicable absence of stability over time of the batches produced, and of reproducibility of stability, since some batches are stable while others are not,
e) the risks of microbial contamination of the final product, and
f) the drop in overall energy efficiency of the purification process, based on poor management of the biomass concentration factor.

SUMMARY OF THE INVENTION

To overcome these drawbacks, the applicant company has chosen to undertake work to implement suitable downstream processing steps, the efficiency of which can be measured:
a) by calculating the protein content and yield of the biomass produced and/or the content of dry biomass, but also
b) by methods of sensory analysis, and/or
c) of measuring the stability over time of the batches produced, by virtue of a quite unique accelerated aging method developed by the applicant company.

The present invention relates to a method for optimizing the downstream processing of a protein-rich biomass of microalgae the *Chlorella* genus which has been prepared beforehand by fermentation in heterotrophic conditions and in the absence of light, comprising:
1) providing a biomass comprising more than 50% proteins by dry weight of biomass;
then, at low temperature:
2) recovering the biomass at the end of fermentation,
3) washing and concentrating the biomass,
4) optionally lyzing the biomass,
then, with no low temperature constraints:
5) optionally concentrating the biomass suspension,
6) applying a heat treatment,
7) drying the resulting biomass, to obtain the product,
a step of adjusting the pH to 7 being applied before or after step 6) of heat treatment.

Preferably, the biomass comprises more than 50% by dry weight of proteins, preferably more than 55%, more preferably still more than 60, 65 or 70%.

When the steps are carried out at low temperature, the temperature is kept lower than 8° C., preferably lower than 4° C. Preferably, this low temperature is applied throughout steps 2) to 4) of the method in accordance with the invention.

Preferably, the heat treatment is a high temperature/short time (HTST) heat treatment for 30 seconds to 5 minutes at a temperature lower than 100° C.

Alternatively, the heat treatment is an ultra-high temperature (UHT) heat treatment at a temperature of between 100° C. and 150° C. for 5 to 30 seconds.

Preferably, the biomass is washed with at most 6 volumes of water per 1 volume of biomass, preferably with at most 3 volumes of water.

Preferably, the biomass suspension is neutralized to pH 7 by adding KOH or NaOH, preferably by adding KOH.

Preferably, the cells of the biomass are lyzed by milling, preferably bead milling.

Preferably, the biomass is concentrated by centrifugation or evaporation.

Optionally, the effects of the steps of processing the microalgal biomass on the quality of the product may be determined by one or more of the following parameters:
measuring the dry cell weight in the biomass;
measuring the sugar content;
determining the amount of proteins;
analyzing the volatile organic compounds;
measuring enzyme activities, in particular lipoxygenase activity;
measuring the coloration or the pigment content;
measuring the content of metals, in particular iron, copper or nickel;
determining the degree of oxidation.

In particular, the effects of several biomass processing operations on the quality of the product are compared and the processing operation(s) giving the best results are selected.

In a particular embodiment, the microalgae of the *Chlorella* genus are chosen from the group consisting of *Chlorella vulgaris*, *Chlorella sorokiniana* and *Chlorella protothecoides*, and are more particularly *Chlorella protothecoides*.

The aim of this method is, in particular, to develop an optimized method for the production of protein-rich microalgal biomass at high yield; said biomass having no undesirable flavors or odors and being stable over time.

DETAILED DESCRIPTION OF THE INVENTION

The present invention relates to an optimized method which allows all the requirements specific to the production of a protein-rich microalgal biomass to be met, more particularly in terms of protein production efficiency, in terms of organoleptic quality and in terms of stability over time of said biomass.

The present invention thus relates to a method for optimizing the downstream processing of a protein-rich biomass of microalgae of the *Chlorella* genus which has been prepared beforehand by fermentation in heterotrophic conditions and in the absence of light, comprising:
1) providing a biomass comprising more than 50% proteins by dry weight of biomass;
then, at low temperature:
2) recovering the biomass at the end of fermentation,
3) washing and concentrating the biomass,
4) optionally lyzing the biomass,
then, with no low temperature constraints:
5) optionally concentrating the biomass suspension,
6) applying a heat treatment,
7) drying the resulting biomass, to obtain the product,
a step of adjusting the pH to 7 being applied before or after step 6) of heat treatment.

According to step 1) of the method in accordance with the invention, the biomass comprises at least 50% by dry weight of proteins. Even more preferably, it comprises at least 55, 60, 65 or 70° by dry weight of proteins.

The preferred microalgae of the invention can grow in heterotrophic conditions (on sugars as source of carbon and in the absence of light). The applicant company recommends choosing protein-rich microalgae of the *Chlorella* genus. The microalgae used may be chosen, nonexhaustively, from *Chlorella protothecoides*, *Chlorella kessleri*, *Chlorella minutissima*, *Chlorella* sp., *Chlorella sorokiniana*, *Chlorella*

*luteoviridis*, *Chlorella vulgaris*, *Chlorella reisiglii*, *Chlorella ellipsoidea*, *Chlorella saccarophila*, *Parachlorella kessleri*, *Parachlorella beijerinkii*, *Prototheca stagnora* and *Prototheca moriformis*. Preferably, the microalgae used according to the invention belong to the species *Chlorella protothecoides*.

In a very particular embodiment, the strain of *Chlorella sorokiniana* is the strain UTEX 1663 from *The Culture Collection of Algae at the University of Texas at Austin*, USA. In a very particular embodiment, the strain of *Chlorella protothecoides* is the strain CCAP211/8D from *The Culture Collection of Algae and Protozoa*, Scotland, UK. The microalgae are cultured in liquid medium to produce the biomass proper. According to the invention, the microalgae are cultured in a medium containing a source of carbon and a source of nitrogen in the absence of light (heterotrophic conditions). The solid and liquid growth media are generally available in the literature, and recommendations for the preparation of particular media suitable for a wide variety of strains of microorganisms may be found, for example, online at www.utex.org/, a site run by the University of Texas at Austin for its culture collection of algae (UTEX). The production of biomass is carried out in fermentors (or bioreactors).

The specific examples of bioreactors, culture conditions and heterotrophic growth and propagation methods may be combined in any appropriate way to improve the efficiency of the microalgal growth and the protein content. The production methods for such a biomass are well known to those skilled in the art.

Steps 2 to 4 of the method in accordance with the invention are carried out at low temperature, that is to say at a temperature kept lower than 8° C., preferably lower than 4° C. This low temperature enables cellular metabolism, and also the development of microbial contaminants, to be stopped/slowed down.

Moreover, as the applicant company has noted, another advantage of carrying out these steps at low temperature is that the cooling, and also the limited oxygenation, promote limitation of the oxidative phenomena which cause "off notes" and which are a source of instability in the final product.

More particularly:

In step 2) of the method in accordance with the invention, the biomass is recovered at the end of the fermentation.

Advantageously, the biomass is recovered as soon as the residual source of nutrition (in particular the residual glucose) is used up.

These conditions enable the production efficiency of the biomass produced to be optimized, and the concentration of residual soluble matter which has to be removed during the washing step to be limited.

In step 3) of the method in accordance with the invention, the biomass is washed and concentrated. The biomass is washed of the residual soluble matter at the end of fermentation (salts, non-metabolized sugars, etc.), by dilution with water.

The biomass is washed with at most 6 volumes of water per volume of biomass, preferably with at most 3 volumes of water per volume of biomass, and in a very particular embodiment with around one volume of water per volume of biomass.

This operation makes it possible to significantly improve the cell purity (reduce the fraction of solids at the end of fermentation which is derived from a non-cellular component).

In this way, the load of this soluble matter, which is potentially a source of degradation of the sensory properties of the biomass, is reduced.

This operation is advantageously carried out in low temperature conditions.

The biomass is then concentrated to 15 to 40% solids, preferably 20-30% solids.

It may be concentrated by centrifugation, for example using an Alfa Laval FEUX 510 centrifuge.

In step 4), the resulting biomass is optionally lyzed.

The cell walls and the intracellular components are milled or reduced.

Various techniques are available for carrying out the lysis, such as microbead milling and high-pressure homogenization technology.

The preferred mode is microbead milling, in particular microbead milling using a Bead Mill. Conventionally, a NETZSCH Labstar bead mill is used with zirconium silicate beads of 0.5 mm diameter. The degree of lysis may be variable. For example, a degree of lysis of 50, 60, 70, 80, 90 or 95% of the cells may be envisioned.

The final three steps of the method in accordance with the invention are carried out with no low temperature constraints.

In step 5), the resulting biomass suspension is optionally concentrated.

The biomass is concentrated by evaporation. Any type of evaporator may be used, for example a rotary evaporator, a forced flow evaporator, a falling film evaporator or a wiped film evaporator.

Concentration by evaporation contributes to improving the concentration factor before drying by optimizing the energy performance of the method. This concentration also makes it possible to strip out any volatile products which are potentially deleterious to the sensory properties of the final product.

In step 6), a heat treatment is applied.

This heat treatment acts as a safety measure to counter any microbiological risks to the final product.

Conventionally it consists of an HTST or UHT treatment. Moreover, this heat treatment contributes to improving the sensory properties of the final product.

Two different types of heat treatment are envisioned in particular.

The first type is a high temperature/short time (HTST) heat treatment of the biomass, for example for 30 seconds to 5 minutes at a temperature lower than 100° C.

The second type is a UHT (ultra-high temperature) heat treatment. Preferably, the UHT heat treatment is carried out at a temperature of between 100 and 150° C. for 5 to 30 seconds, preferably at a temperature of between 120 and 140° C. for 5 to 15 seconds.

In step 7), the resulting biomass is dried to obtain the product.

Preferably, the drying is carried out by spray drying.

Spray drying is carried out in a spray dryer in which a liquid suspension is sprayed, in the form of a dispersion of fine droplets, into a stream of heated air, with the material carried along being rapidly dried and forming a dry powder.

There are many devices in the prior art for spray drying lipid-rich compounds. It is possible to readily find in the literature illustrations of the equipment and technology proposed: for example, in the Spray Drying Handbook by K. Masters, in particular in the $5^{th}$ edition thereof, published in 1991 and republished in 1994 by Longman Scientific & Technical (available at the British Library or the Library of Congress under ISBN 0-470-21743-X), or in the BETE® Spray Dry Manual, 2005 (accessed at the website www.bete.com).

For example, the spray drying may be carried out on a Niro Mobile Minor single-effect spray drying tower or on a Filtermat FMD125 with cyclone.

A final, key step consists in neutralizing the pH of the (lyzed or not lyzed) biomass suspension to 7 before or after step 6) of heat treatment.

This neutralization may be carried out by adjusting the pH to 7 by adding NaOH or KOH, preferably KOH. This neutralization with concentrated potassium hydroxide makes it possible to smooth out any possible fluctuations in pH downstream and between production batches, and also to improve the sensory properties.

The addition of one or more antioxidants may also be chosen (before or after the step of neutralizing the pH to 7).

It is possible, advantageously, to choose ascorbic acid and/or a mixture of tocopherols, preferably a combination of ascorbic acid and tocopherols.

Conventionally, the proportions used are 150 ppm/dry of ascorbic acid and 500 ppm/dry of a mixture of tocopherols (xppm/dry meaningxmg per kg of dry biomass).

It is clearly understood that the nature of the antioxidant depends on the properties of the matrix to be stabilized. They must improve the stability of the final product with regard to the risks of oxidative modification, and thereby improve the preservation of the final product by retaining a stable physicochemical and sensory profile.

The effects of the steps of processing the microalgal biomass on the quality of the product may moreover be determined by:
- measuring the loss of yield, in particular analyzing the loss of cellular solids and also the loss in protein content arising in particular from "dissolution" during the heat treatment and the elimination thereof upon washing, if the latter step is carried out downstream. It has been shown that this loss of solids predominantly consists of a protein fraction (which allows the difficulties a) and b) identified above to be addressed);
- determining the sensory quality of the batches produced, in particular by a sensory panel formed to evaluate the sensory properties of various batches (to address difficulty c));
- measuring stability over time, in particular by an accelerated aging test consisting of comparative sensory analysis of the initial sample and of this same sample placed in an oven under hermetic conditions for 10 days at 60° C. (to address difficulty d)). The sensory analysis is carried out in accordance with the test described. This analysis makes it possible to highlight any oxidation descriptors, thereby making it possible to evaluate the stability of the sample with regard to this oxidative degradation;
- measuring the change in microbial load over time on the various steps of the method (to address difficulty e));
- analyzing the change in the solids (concentration factor) over this series of operations (to address difficulty f)).

Three characteristics essential to evaluating the quality have been defined by the applicant company:
- the content of dry biomass and/or proteins in the product;
- the organoleptic quality of the product; and
- the stability over time of the product.

Moreover, other parameters may also be taken into account for evaluating the quality of the product, in particular the following:
- measuring the dry cell weight in the biomass;
- measuring the sugar content;
- determining the amount of proteins;
- analyzing the volatile organic compounds;
- measuring enzyme activities, in particular lipoxygenase activity;
- measuring the coloration or the pigment content;
- measuring the content of metals, in particular iron, copper or nickel;
- determining the degree of oxidation.

The invention will be better understood by virtue of the following examples which are intended to be non-limiting and illustrative.

EXAMPLES

Several batches were produced by downstream processing of a biomass of *Chlorella protothecoides* prepared by fermentation in heterotrophic conditions and in the absence of light. The strain used is *Chlorella protothecoides* with the reference UTEX 250.

The various steps were carried out as defined below.

HTST treatment: high temperature/short time (HTST) heat treatment of the biomass, for 30 seconds to 5 min, at a temperature lower than 100° C., in particular for 1 minute at 75° C.

Washing: with at most 6 volumes of water per volume of biomass.

Addition of antioxidant: addition of ascorbic acid and of a mixture of tocopherols, preferably with proportions of 150 ppm/dry of ascorbic acid and 500 ppm/dry of a mixture of tocopherols.

Spray drying: spray drying on a Niro Mobile Minor single-effect spray drying tower or on a Filtermat FMD125 with cyclone.

Milling: bead milling using a Bead Mill. Conventionally, a NETZSCH Labstar bead mill is used with zirconium silicate beads of 0.5 mm diameter.

Concentrating: concentration/evaporation by rotary evaporator (laboratory scale) or any other type of larger-scale evaporator (forced flow, falling film, wiped film, etc.) of 20 to 30% solids.

UHT treatment: at a temperature of between 100 and 150° C. for 5 to 30 seconds, preferably at a temperature of between 120 and 140° C. for 5 to 15 seconds.

The quality of the batches obtained is studied in the following way. One or more of the following parameters were determined or measured.

Sensory quality: the sensory quality of the batches produced is evaluated by a sensory panel of approximately 18 people for a set of sensory descriptors. The expert panel evaluates the olfactory properties of the batches at 3% in water and at 55° C. (samples presented in a closed glass jar), on ordinal intensity scales (NF V 09-015:1985).

Stability over time: this is measured during an accelerated aging test developed by the applicant company which consists of a comparative sensory analysis of the initial sample and of this same sample placed in an oven under hermetic conditions for 10 days at 60° C. The sensory analysis makes it possible to highlight any oxidation descriptors, thereby making it possible to evaluate the stability of the sample with regard to this oxidative degradation.

Measuring the Loss of Yield:
- measuring the dry cell weight (DCW) and/or
- measuring the dry biomass and/or
- the protein content.

Moreover, additional parameters may also be evaluated.

Sugar content: determining the sugar (glucose, maltose, fructose, sucrose) content by liquid chromatography. Following separation by ion exchange chromatography, the various species are detected by amperometric analysis.

Volatile organic compounds: the content of volatile organic compounds is determined by SPME/GC.

Analysis of the heat treatment: by observing, by optical microscopy, changes brought about in cell morphology.

Measuring the coloration: measuring, by means of a spectrocolorimeter, reflectance measurements at wavelengths from 400 nm to 700 nm under the D65 or C illuminant and with the CIE 1931 2° observer. The indices "L", "a" and "b" are determined, where "L" corresponds to lightness, "a" to the green to red scale and "b" to the blue to yellow scale.

Pigment content: after breaking the cells open, the pigments are extracted with 90% acetone. The extract is then analyzed by spectrophotometry. The pigments are quantified by calculations based on the absorbances recorded at various wavelengths.

Assaying of metals: destruction of the organic material by mineralization using a sulfonitric mixture and subsequent determination by emission spectrometry following appropriate dilution.

Determining the degree of oxidation: after dilution in isooctane, measurement of the absorbance at 232 nm.

The invention claimed is:

1. A method for optimizing the downstream processing of a protein-rich biomass of microalgae of the *Chlorella* genus which has been prepared beforehand by fermentation in heterotrophic conditions and in the absence of light, comprising:
   1) providing a fermentation broth comprising biomass, said biomass comprising more than 55% protein by dry weight;
   2) chilling the fermentation broth to lower than 8° C. and recovering the biomass;
   3) washing and concentrating the biomass;
   4) optionally lysing the biomass;
   5) optionally concentrating the lysed biomass;
   6) applying a heat treatment; and
   7) drying the resulting biomass to obtain the product.

2. The method as claimed in claim 1, characterized in that the protein comprises more than 60% by dry weight of the biomass.

3. The method as claimed in claim 1, characterized in that the heat treatment is a high temperature/short time (HTST) heat treatment for 30 seconds to 5 minutes at a temperature lower than 100° C.

4. The method as claimed in claim 1, characterized in that the heat treatment is an ultra-high temperature (UHT) heat treatment at a temperature of between 100° C. and 150° C. for 5 to 30 seconds.

5. The method as claimed in claim 1, characterized in that the biomass is washed with at most 6 volumes of water per 1 volume of biomass.

6. The method as claimed in claim 1, characterized in that the fermentation broth is neutralized to pH 7 by adding KOH or NaOH.

7. The method as claimed in claim 1, characterized in that the cells of the biomass are lysed by milling.

8. The method as claimed in claim 1, characterized in that the biomass is concentrated by centrifugation or evaporation.

9. The method as claimed in claim 1, characterized in that the effects of the steps of processing the microalgal biomass on the quality of the product are also determined by one or more of the following parameters:
   a) measuring the dry cell weight in the biomass;
   b) measuring the sugar content;
   c) determining the amount of proteins;
   d) analyzing the volatile organic compounds;
   e) measuring the enzyme activities;
   f) measuring the coloration of the pigment content;
   g) measuring the content of metals; and/or
   h) determining the degree of oxidation.

10. The method as claimed in claim 1, characterized in that the microalgae of the *Chlorella* genus are selected from the group of species consisting of *Chlorella vulgaris*, *Chlorella sorokiniana* and *Chlorella* protothecoides.

11. The method as claimed in claim 10, characterized in that the microalgae are of the species *Chlorella protothecoides*.

12. The method as claimed in claim 9, wherein the enzyme activities comprise lipoxygenase activity.

13. The method as claimed in claim 9, wherein the metals comprise iron, copper and/or nickel.

* * * * *